United States Patent [19]

Mullins et al.

[11] Patent Number: 5,264,538
[45] Date of Patent: Nov. 23, 1993

[54] CYCLIC POLY(ARYL ETHER) OLIGOMERS

[75] Inventors: Michael J. Mullins; Edmund P. Woo; Kimberly E. Balon; Daniel J. Murray; Cheng-Cheng C. Chen, all of Midland, Mich.

[73] Assignee: The Dow Chemical Company, Midland, Mich.

[21] Appl. No.: 544,718

[22] Filed: Jun. 27, 1990

Related U.S. Application Data

[63] Continuation-in-part of Ser. No. 393,503, Aug. 14, 1989, abandoned.

[51] Int. Cl.$^5$ .................. C08G 2/00; C08G 75/00
[52] U.S. Cl. ...................... 528/226; 528/125; 528/126; 528/128; 528/167; 528/170; 528/171; 528/174; 528/175; 528/206; 528/220; 548/417; 548/418; 548/419; 548/423; 549/11; 549/12; 549/349; 549/354
[58] Field of Search ............... 528/125, 126, 128, 167, 528/170, 171, 174, 175, 206, 220, 226; 549/11, 12, 349, 354; 548/423, 417–419

[56] References Cited

U.S. PATENT DOCUMENTS

| | | | |
|---|---|---|---|
| 4,136,087 | 1/1979 | Williams, III et al. | 528/79 |
| 4,740,583 | 4/1988 | Brunelle et al. | 528/370 |
| 4,794,155 | 12/1988 | Woo et al. | 528/125 |
| 4,851,455 | 7/1989 | Job et al. | 525/132 |
| 4,880,884 | 11/1989 | Mullins et al. | 525/549 |
| 5,110,893 | 5/1992 | Fukuyama | 528/125 |

FOREIGN PATENT DOCUMENTS

| | | | |
|---|---|---|---|
| 0317226 | 5/1989 | European Pat. Off. | 549/10 |
| 2-264771 | 10/1990 | Japan. | |
| 1226882 | 9/1989 | United Kingdom | 549/11 |

OTHER PUBLICATIONS

Cella et al., Ring Opening Polymerization of Cyclic Ethers & Thioethers, Amides, Sulfones via aromatic ether—ether exchange; Amer. Chem. Soc. Polymer Prep., vol. 30, No. 2 (1989), pp. 142–143.

Cella, et al., Poly. Prepr.30(2), 581–582, (Sep. 1989).

*Primary Examiner*—John Kight, III
*Assistant Examiner*—P. Hampton-Hightower
*Attorney, Agent, or Firm*—Douglas N. Deline

[57] ABSTRACT

Cyclic poly(aryl ether) oligomers and mixtures thereof, and methods for the preparation thereof in a highly dilute reaction medium under reaction conditions favorable for ring closure at low degrees of polymerization. These oligomers are represented by the general formula

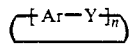

where each Y is divalent oxygen or divalent sulfur, each Ar is an aromatic diradical which comprises one or more $C_6$ to $C_{20}$ arylene groups and has at least one electron withdrawing group attached to an aromatic ring, and n is an integer from 1 to about 20 with the proviso that for integer values of n equal to 1 or 2 all linkages between independent aromatic rings comprise at least one atom.

13 Claims, No Drawings

CYCLIC POLY(ARYL ETHER) OLIGOMERS

This is a continuation-in-part of U.S. application Ser. No. 393,503, filed Aug. 14, 1989, hereby incorporated by reference, and now abandoned.

Background of the Invention

1. Field of the Invention

This invention relates to cyclic poly(aryl ether) oligomers, and to methods for the preparation of such oligomers. More particularly, this invention relates to a general method with features which permit the preparation of a broad class of cyclic poly(aryl ether) oligomers from a variety of starting materials.

2. Description of Related Art

The use of thermoplastic resins to prepare composites has received considerable attention in recent years. An important advantage of thermoplastic composites relative to those based on thermosets is excellent retention of mechanical properties after impact.

An important disadvantage of thermoplastic composites is the cost of manufacture of small numbers of finished parts. Molds and autoclaves suitable for the high temperature and pressure required are expensive. In addition, the high melt viscosity of thermoplastics causes considerable difficulties in the coating of fibers without the formation of voids, which are detrimental to the mechanical properties of the composite.

One solution to this problem is to prepare a cyclic precursor which ring opens upon heating with a catalyst in the mold. Ring opening polymerizations are desirable for this application in that there are no co-products which must be removed.

An example well known in the art of the use of a cyclic precursor which ring opens upon heating with a catalyst in a mold is that of caprolactam. In this application caprolactam is used as a low viscosity monomer for the preparation of nylon 6, an aliphatic polyamide. A second example, described by Burnelle, et al., in U.S. Pat. No. 4,644,053 (1987) is the polymerization of cyclic carbonates of Bisphenol A, (2,2'-bis(4-hydroxyphenyl)-propane).

A consideration for many composite applications is that they need resistance to high temperatures, humid environments, and chemicals such as fuels, hydraulic fluids, and cleaning solvents. The aforementioned aliphatic polyamide and Bisphenol A polycarbonate do not have the necessary combination of properties. Poly(aryl ethers) are an important class of thermoplastic resins employed for the manufacture of composites which do meet the above requirements. Therefore, a low viscosity precursor to poly(aryl ether) thermoplastics would be highly desirable for the manufacture of composites.

The prior art related to the production of what are generally referred to as polyarylene polyethers is rich indeed, in terms of the multitude of various polymers that fall under this classification, as well as the various methods for their production. U.S. Pat. No. 4,175,175 describes polyarylene polyethers that are linear thermoplastic reaction products of an alkali metal double salt of a dihydric phenol and a dihalobenzenoid compound. These polymers are characterized by high molecular weights and by high melt viscosities. Related polyarylene polyethers are described in U.S. Pat. Nos. 4,777,235 and 4,783,520. U.S. Pat. Nos. 4,051,109 and 4,232,142 relate to the production of polyarylene ether sulfones and ketones through the use of salts of various precursors. U.S. Pat. Nos. 4,065,437 and 3,832,331 relate to aromatic polyether-sulfones. Other related art in this field is found in U.S. Pat. Nos. 4,036,815, 4,113,699, 3,418,277, 4,056,511, 4,400,499, 3,446,654, Re. 28,252, and 4,711,945.

EP 317,226 discloses macrocyclic compounds, including cyclic ethers, containing polyarylene units and other cyclic units. WO 88/06605 discloses random macrocyclic monomer and oligomer compounds containing a spiro(bis)indane moiety.

SUMMARY OF THE INVENTION

The general objective of this invention is to prepare novel cyclic poly(aryl ether) oligomers, which are characterized by low melt viscosities, and which are suitable for ring opening polymerizations. Each mention of the term ether should be understood to include thioether as well. These cyclic poly(aryl ether) oligomers contain one or more (Ar-Y) repeating units and are represented by the formula

where each Y is divalent oxygen or divalent sulfur, each Ar is an aromatic diradical which comprises one or more $C_6$ to $C_{20}$ arylene groups and has at least one electron withdrawing group attached to an aromatic ring, and n is an integer from 1 to about 20 with the proviso that for integer values of n equal to 1 or 2 all linkages between independent aromatic rings comprise at least one atom.

The aromatic diradical may be quite simple, consisting of a single arylene group with only one aromatic ring, and one electron withdrawing group attached to the aromatic ring. In other embodiments the aromatic diradical is more complex and may contain more than one arylene group. The arylene groups contain from 6 to 20 carbon atoms and one or more aromatic rings.

The electron withdrawing group in one embodiment is monovalent, and, thus, pendant from an aromatic ring. In another embodiment the electron withdrawing group is divalent and in the backbone of the ring. In further more complex embodiments of the present invention the divalent electron withdrawing groups comprise various combinations of electronegative groups and arylene groups.

The aromatic diradical may also contain one or more linking groups in the backbone of the ring which are heterocycles or groups of heterocycles.

The cyclic poly(aryl ether) oligomers of the present invention are prepared by the addition of the reactants as solutions to a reaction medium that dilutes and disperses the reactants. Reaction times as long as seven days have been used, but in most cases the cyclization reactions is favorable enough that a point of dimishing returns is reached in a much shorter time, often within one day or less.

A variety of starting materials and different reactions can be used in this general method of preparation. Under the reaction conditions of the general method of preparation of the present invention the lifetimes of any intermediates formed is short, with ring closure being favored. The ultimate yield of cyclic poly(aryl ether) oligomers is high.

These cyclic poly(aryl ether) oligomers can be prepared by several specific novel methods which are modifications of the methods described in the prior art which are used to prepare high molecular weight linear polymers. Whereas the prior art preparative methods are generally characterized by batchwise addition of the various reactants and high reactant concentrations, the preparative methods of the present invention are characterized by gradual addition of the reactants over a period of time. The reaction conditions are such that when the reactants are brought into contact ring-forming intermediates are immediately produced.

These conditions provide an environment in which any reactive intermediate preferably undergoes ring closure at a relatively low degree of polymerization, with n no more than about 20, more preferably no more than about 10, rather than continuing polymerization linearly to form a high molecular weight polymer. In cases where the systhetic procedure results in an intermediate which itself is a relatively long structure, ring closure may be favored for a single unit, with the result that n is 1. It should be understood that the term "oligomer" is meant to include these cases where n is 1, or where there is a mixture of oligomers with different n values including n equal to 1.

The cyclic poly(aryl ether) oligomers prepared in this fashion can then be isolated either as a mixture of oligomers or separated into individual oligomers. For some starting materials and methods of preparation under appropriate reaction conditions, a single oligomer may predominate as the reaction product. These products have superior characteristics for the production of composites and coatings.

These low melt viscosity cyclic poly(aryl ether) oligomers may be catalytically converted to high molecular weight poly(aryl ethers) which are noted for high temperature stability and solvent resistance. These cyclic oligomers are useful for preparing shaped articles where the high melt viscosities typical of high molecular weight linear poly(aryl ethers) are undesirable.

These cyclic oligomers are useful also for the preparation of protective coatings and adhesives, and for various electronics applications, such as passivation.

The methods of this invention may be used to prepare cyclic poly(aryl ether) oligomers, which polymerize to form high molecular weight polymers which are substantially identical to those present in various commercial products. These commercial products are prepared by prior art methods in which low molecular weight starting materials react to produce high molecular weight linear products. Some examples are ICI's Victrex® PES (polyether sulfone), Amoco's Udel® and Radel® polysulfone, GE's Ultem® polyetherimide, ICI's Victrex® PEEK (poly ether ether ketone) and BASF's Ultrapek® polyetherketone.

DESCRIPTION OF THE PREFERRED EMBODIMENTS

The cyclic poly(aryl ether) oligomers of the present invention are most simply represented by the formula

 (1)

where each Y is divalent oxygen or divalent sulfur, each Ar is an aromatic diradical which comprises one or more $C_6$ to $C_{20}$ arylene groups and has at least one electron withdrawing group attached to an aromatic ring, and n is an integer from 1 to about 20 with the proviso that for integer values of n equal to 1 or 2 all linkages between independent aromatic rings comprise at least one atom.

The aromatic diradical Ar has at least one electron withdrawing group attached to an aromatic ring. Some suitable monovalent groups are —CN, —NO$_2$, —CHO, —CO$_2$R, —CO$_2$NH$_2$, —P(O)(OR)$_2$, —P(O)R$_2$, —$^+$NR$_3$, —$^+$SR$_2$, —F and —CF$_3$.

In another aspect of the present invention the electron withdrawing group is divalent and in the backbone of the ring. In a preferred embodiment the divalent electron withdrawing group comprises an electronegative group Z which is —SO$_2$—, —CO—, —CONH—, —CONR—, —$^+$NR$_2$—, —$^+$PR$_2$—, —$^+$SR—, —P(O)R—, —C$_6$F$_4$—, —C$_6$F$_4$C$_6$F$_4$—, —C(CF$_3$)$_2$—, —CHCH—, —N=N—, —CNNCH—, where R is a hydrocarbyl radical of 1 to 12 carbon atoms, imidazole, oxazole, pyrazole, isoxazole or oxapyrazole, and the cyclic poly(aryl ether) oligomer is represented by the formula

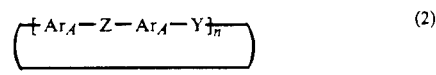 (2)

where Y and n are as previously defined and each Ar$_A$ is an arylene group containing at least one aromatic ring.

The arylene group Ar$_A$ contains from 6 to 20 carbon atoms and one or more aromatic rings, through which it is incorporated into the ring of the oligomer. In more complex arylene groups independent aromatic rings are linked by divalent linking groups such as —O—, —S—, Z as defined above, and simple hydrocarbyl groups. For oligomers with values of n equal to 1 to 2 all linkages between independent aromatic rings comprise at least one atom, but for others it may be a direct bond. Some preferred arylene groups are phenylene and substituted phenylene, and the following complex arylene groups:

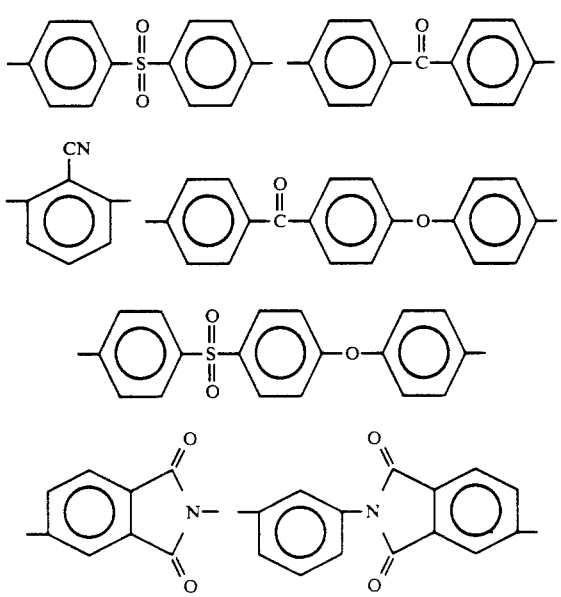

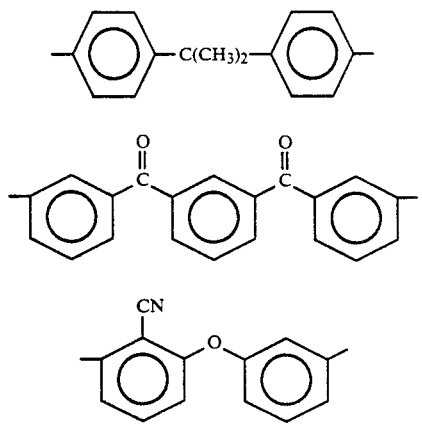

In other embodiments the electron withdrawing group attached to Ar may comprise several independently selectable Z groups and several independently selectable $Ar_A$ groups.

The aromatic diradical may additionally contain one or more linking groups L in the backbone of ring where preferred examples of suitable linking groups include the following:

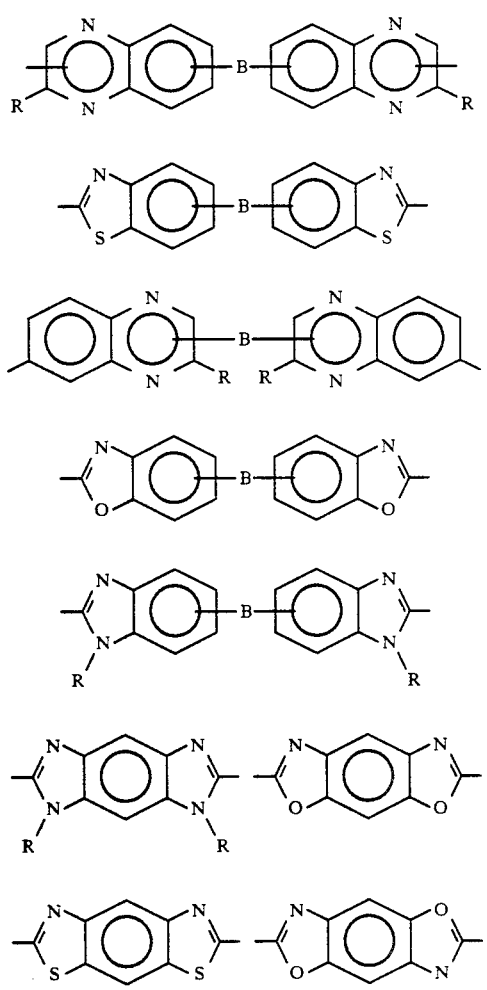

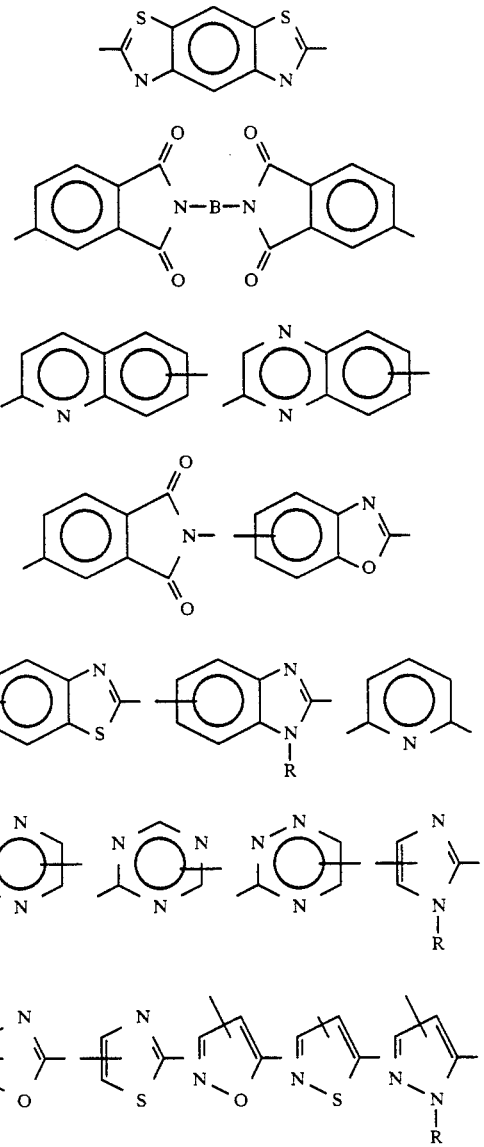

where R is a $C_1$ to $C_{12}$ hydrocarbyl radical and each of the heterocycles may be additionally substituted with one or more $C_1$ to $C_{12}$ hydrocarbyl radical, halogens, $C_1$ to $C_{12}$ alkoxy or aryloxy radicals, cyano, nitro, alkylcarbonyl, formyl, alkoxycarbonyl or aryloxycarbonyl, arylsulfonyl; B is in each occurrance a direct bond, —O—, —S—, —SO₂—, a carbonyl, a phosphinyl, a phosphine oxidyl, a tertiary aminyl, and a $C_1$ to $C_{24}$ hydrocarbyl radical optionally substituted with halogens, $C_1$ to $C_{12}$ alkoxy or aryloxy radicals, cyano, nitro, alkylcarbonyl, formyl, alkoxycarbonyl or aryloxycarbonyl, arylsulfonyl, or carbonylarylcarbonyl.

In many cases a desirable embodiment of the present invention is a composition comprising a mixture of cyclic poly(aryl ether) oligomers as represented by formula (1), which encompass the specific subgroups discussed up to now. A preferred embodiment is such a composition wherein the cyclic poly(aryl ether) oligomers of the mixture are represented by one or more of formulas I-XI

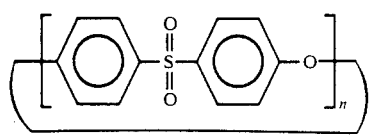 I
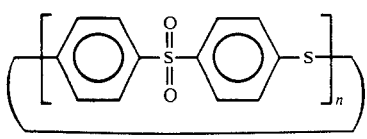 II
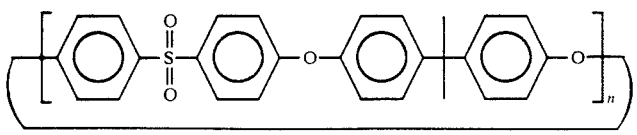 III
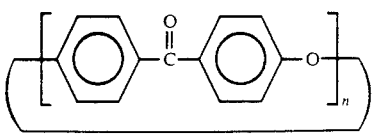 IV
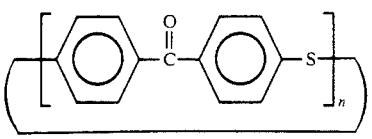 V
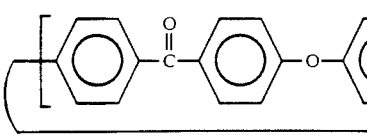 VI
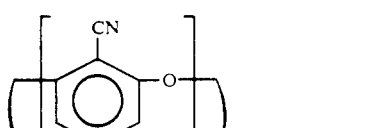 VII
 VIII
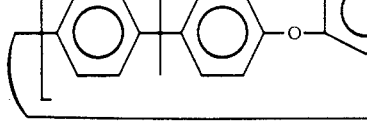 IX
+
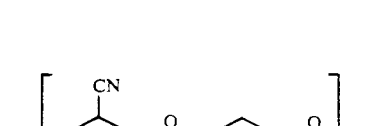 X

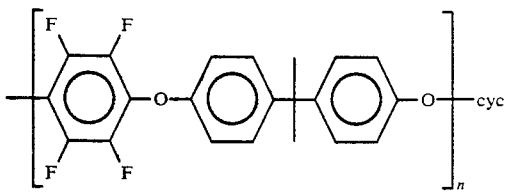

The term "cyc" in association with a structure indicates a cyclic structure.

is an abreviation used in structural formulas to conveniently represent —C(CH$_3$)$_2$—, as in a bisphenol A nucleus.

Especially preferred embodiments are those wherein the cyclic poly(aryl ether) oligomers of said mixture are represented by

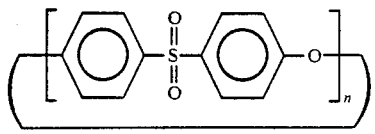

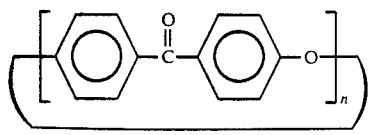

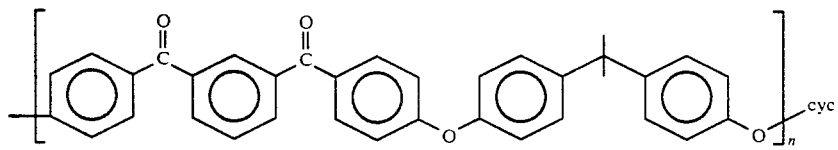

IX

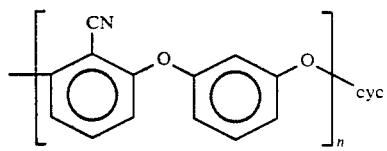

X

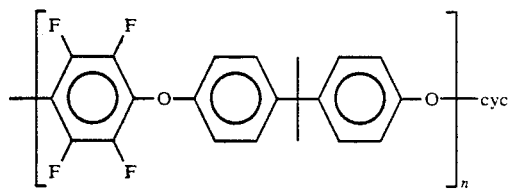

XI

An example of a more complex embodiment of the present invention is that represented by the formula

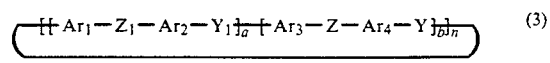 (3)

where Z, Y and n are as previously defined; Y$_1$ is divalent oxygen or divalent sulfur independently selectable from Y; Ar$_1$, Ar$_2$, Ar$_3$ and Ar$_4$ are arylene groups independently selected from the group consisting of Ar$_A$; Z$_1$ is independently selectable from the group consisting of Z; and a and b are integers of from 1 to 3. In formula 3 a and b indicate the ratio of the blocks and are not meant to be indicative of any ordering of blocks in this embodiment.

Preferred embodiments which correspond to formula (3) are

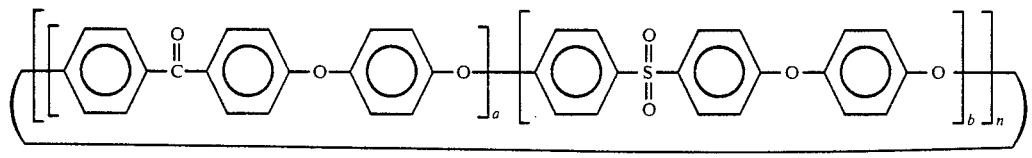

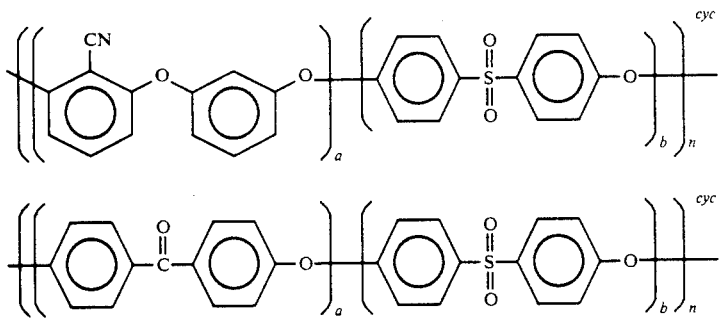

Another embodiment is that of a composition comprising a mixture of oligomers corresponding to formula (3), including the specific example given above, either alone or in admixture with some other cyclic poly(aryl ether) oligomer.

Another complex embodiment corresponds to formula (4)

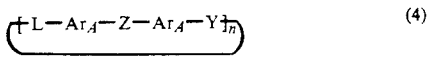

where Y, n, Z, $Ar_A$, and L are as previously defined.

Still another embodiment of the present invention is a composition which comprises a mixture of at least 10% of one or more cyclic poly(aryl ether) oligomers represented by the formula:

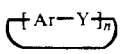

and up to 90% of one or more linear poly(aryl ether) polymers wherein the repeating unit is:

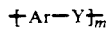

where Ar, Y and n are as previously defined, and m is an integer greater than 20. Admixture of the low melt viscosity oligomers of the present invention with high melt viscosity linear polymers lowers the viscosity of the composition so formed which is desirable in many applications.

Many of the methods described in the prior art for the production of high molecular weight poly(aryl ethers) can be modified according to the principles of the present invention and used to produce cyclic poly(aryl ether) oligomers. In particular, three methods will be described for producing these materials. In the first method an activated aryl dihalide is reacted with an aromatic diol in the presence of a base. An activated aryl dihalide as used herein is defined as an aryl dihalide which has attached to the aromatic ring at least one electron withdrawing group other than the two halide leaving groups. The prior art is replete with discussions concerning activated aryl dihalides. Examples of preferred activated aryl dihalides include 4,4'-difluorobenzophenone, 4,4'-dichlorobenzophenone, 4,4'-dinitrobenzophenone, bis-(4-fluorophenyl)sulfone, bis-(4-chlorophenyl)sulfone, bis-(4-chloro-3-nitrophenyl)sulfone, 4,4'-dichloroazobenzene, 4,4'-dichloroazoxybenzene, 1,3-bis-(4-fluorobenzoyl)benzene, 1,4-bis-(4-fluorobenzoyl)benzene, 1,3-bis-(4-chlorobenzoyl)benzene, 1,4-bis-(4-chlorobenzoyl)benzene, 2,6-difluorobenzenenitrile, 2,4-difluorobenzenenitrile, 2,6-dichlorobenzenenitrile, 2,4-dichlorobenzenenitrile, and hexafluorobenzene.

Examples of preferred diols include 1,2-ethanediol, 1,2-propanediol, 1,3-propanediol, 1,4-butanediol, 1,4-cyclohexanediol, 1,4-bis-(hydroxymethyl)benzene, 1,3-dihydroxybenzene, 1,4-dihydroxybenzene, 1,4-dihydroxy-2-methylbenzene, 1,6-dihydroxynaphthalene, 2,6-dihydroxynaphthalene, bis-(4-hydroxyphenyl)-phenylmethane, bis-(4-hydroxyphenyl)-diphenylmethane, 1,1-bis-(4-hydroxyphenyl)ethane, 1,2-bis-(4-hydroxyphenyl)ethane, 2,2'-bis-(4-hydroxyphenyl)propane, 1,1,1,3,3,3-hexafluoro-2,2'-bis-(4-hydroxyphenyl)propane, 1,1-bis-(4-hydroxyphenyl)-acetonitrile, 1,3-bis-(4-hydroxybenzoyl)benzene, 1,4-bis-(4-hydroxybenzoyl)benzene, bis-(4-hydroxyphenyl)methane, bis-(4-hydroxyphenyl)sulfone, bis-4-hydroxyphenyl)sulfide, bis-(4-hydroxyphenyl)ether, 4,4'-dihydroxybenzophenone, 4,4'-dihydroxybiphenyl, 4,4'-dihydroxyazobenzene, 4,4'-dihydroxyazoxybenzene, bis-(4-mercaptophenyl)ether, bis-(4-mercaptophenyl)sulfide, 3-mercaptophenol, 4-mercaptophenol, 1,3-dimercaptobenzene, 1,4-bis-(4-hydroxycumenyl)benzene and 1,4-dimercaptobenzene.

The second method for the preparation of cyclic poly(aryl ether) oligomers is similar to the first method except that no aromatic diol is used.

In any of the methods for preparation of cyclic poly(aryl ether) oligomers of the present invention where the basic role of the dihalide in the reaction is that of providing a halide leaving group, that role can be performed with compounds containing other leaving groups. The dinitro compounds corresponding to the mentioned dihalides are especially suitable as reactants in these methods. Therefore, although the discussion has been centered around dihalides and the other halide containing reactants, it should be understood that analogous reactants with other leaving groups, especially dinitro compounds, can be used.

Both methods ultimately lead to the same reactive intermediate, which is a linear oligomer capped with a halide at one end and a metal phenate at the other. In actual practice both of these methods are single step procedures.

Schemes I, II and III, below, schematically show these two methods, labeled as Method A and Method B, for three types of starting materials leading to the indicated reactive intermediates which then immediately go on to form the cyclic poly(aryl ether) oligomer products.

Scheme I
Cyclic Poly(aryl ether) Preparation

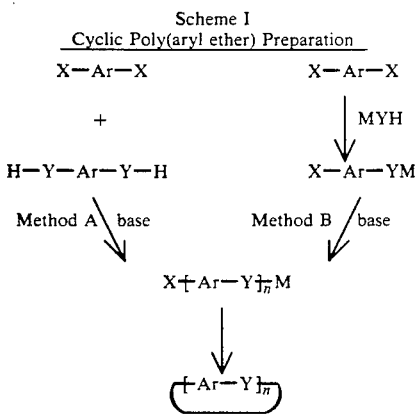

where Ar and Y are as previously defined, X is halide, X-Ar-X is an activated aryl dihalide, H-Y-Ar-Y-H is an aromatic diol or thiol, MYH is a base containing a metal M, X-Ar-YM is the mono salt produced by initial reaction of an activated aryl dihalide and the base,

is the intermediate linear oligomer capped with a halide at one end and a metal phenate at the other, n is from 1 to about 20, and

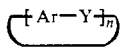

is the cyclic poly(aryl ether) oligomer.

Scheme II
Cyclic Poly(aryl ether) Preparation

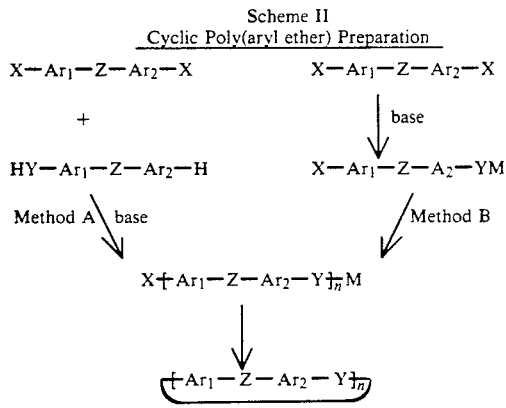

where $Ar_1$, $Ar_2$, Z, X, Y, M and n are as previously defined.

Scheme III
Cyclic Poly(aryl ether) Preparation
Method A

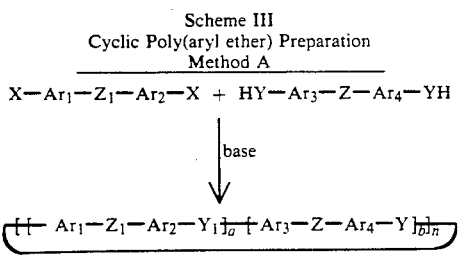

where Z, Y and n are as previously defined; $Y_1$ is divalent oxygen or divalent sulfur independently selectable from Y; $Ar_1$, $Ar_2$, $Ar_3$ and $Ar_4$ are arylene groups independently selected from the group consisting of $Ar_4$; $Z_1$ is independently selectable from the group consisting of Z; and a and b are integers of from 1 to 3. Examples of useful starting materials include 4-fluorophenyl-4-hydroxyphenyl sulfone, 4-chlorophenyl-4-hydroxyphenyl sulfone, 4-fluoro-4'-hydroxybenzophenone, 4-chloro-4'-hydroxybenzophenone, 4-fluoro-3'-hydroxybenzophenone, 4-chloro-3'-hydroxybenzophenone, 1-(4-fluorophenyl)-3-(4-hydroxyphenyl)benzene, 1-(4-fluorophenyl)-4-(4-hydroxyphenyl)benzene, 2-hydroxy-6-fluorobenzenitrile, 2-hydroxy-4-fluorobenzenenitrile, 2-hydroxy-6-chlorobenzenenitrile, 2-hydroxy-4-chlorobenzenenitrile.

Scheme I shows the most general situation, where the electron withdrawing group could be a wide range of mono- and divalent radicals. Scheme II shows the situation where the electron withdrawing group itself contains an aromatic diradical, which would be the case for many materials of interest. In principle, $Ar_1$ and $Ar_2$ are independently selectable, although they may often be identical. Scheme III shows a situation where the cyclic oligomer contains a repeating unit derived from the dihalide that is different from the one derived from the repeating unit from the diphenol, both of which contain an aromatic diradical in the electron withdrawing group. In this case $Ar_1$-$Ar_4$ may all be the same or different in any combination, the electronegative groups Z and $Z_1$ may be the same or different, and Y and $Y_1$ may be the same or different. Method A must be used to produce this type of product where the various groups are different, rather than Method B.

The possible values for n and the distribution of molecular weights for the intermediates and products shown in these schemes can vary depending on a number of experimental variables such as concentration, temperature, starting material stoichiometry, and other factors. As used in this discussion the term oligomer refers to products in which n is from 1 to about 20. Although, technically speaking, when n is equal to 1 there is no "repeat" unit. However, when the aromatic diradical of formula (1) Ar is complex and, thus, quite long, the considerations for ring closure of the intermediate are similar to the situation where the intermediate is made up of several simple repeat units.

Ring closure is favored by low concentrations of reactants and, thereby, low concentrations of intermediates, and by high temperatures which increase the reaction rate of the ring closure reaction. Activated aryl dihalides wherein the two halide leaving groups are fluoride are preferred, since these have faster reaction rates in comparison to the corresponding chlorides or bromides.

In a particular example shown below, the aromatic group of the dihalide (F-Ar-F) and that of the diol (HO-Ar-OH) are identical.

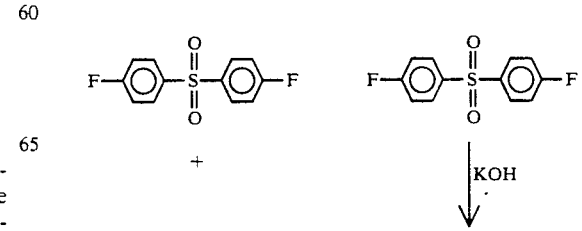

-continued

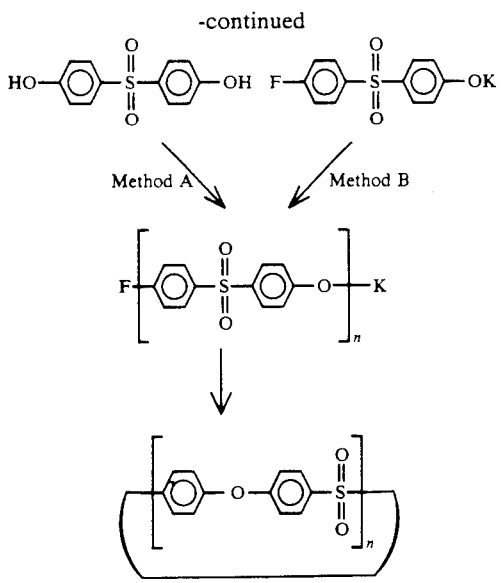

In such circumstances, Method B is preferred as cyclic structures with even and uneven numbers of repeating units (n=3, 4, 5 . . .) are formed. Smaller rings (n=1 or 2) are too strained to be formed in measurable amounts in this specific example, although for some other materials where the electron withdrawing group is longer and more complex there can be significant amounts of the cyclic ether with n=1. Using Method A only cyclic structures of even numbers of repeat units starting with n=4 are formed for this specific example.

Method A is useful for preparations of cyclic poly(aryl ethers) with the repeating unit -$Ar_1$-Z-$Ar_2$-Y-where the two arylene groups are non-identical. For example, the dihalide F-$C_6H_4$-$SO_2$-$C_6H_4$-F would condense with HO-$C_6H_4$-C($CH_3$)$_2$-$C_6H_4$-OH (Bisphenol A) to give cyclic-($C_6H_4$-$SO_2$-$C_6H_4$-O-$C_6H_4$-C($CH_3$)$_2$-$C_6H_4$-O)$_n$.

A third method of preparation, Method C, is to independently prepare an oligomer capped with an activated halide at one end and a phenol at the other, and react it with a base such as an alkali metal hydroxide as follows, where M is an alkali metal, e and f are integers greater than 0, and the other symbols are as indicated hereinabove:

Method C

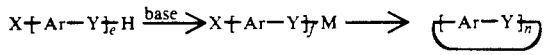

As mentioned before, an "activated" aryl halide as used herein is defined as a halide which is attached to an aromatic ring which is substituted with an electron withdrawing group. One common electron withdrawing group is the sulfone (—$SO_2$—) group. Other examples of divalent electron withdrawing groups are —CO—, —CONH—, —CONR—, —$^+NR_2$—, —$^+P$-$R_2$—, —$^+SR$—, —P(O)R—, —$C_6F_4$—, —$C_6F_4C_6F_4$—, —C($CF_3$)$_2$—, —CHCH—, —N=N—, —CHNNCH—, etc., where R is $C_1$-$C_{12}$ hydrocarbyl radical, as well as electron withdrawing heterocycles such as imidazoles, oxazoles, pyrazoles, isoxazoles, and oxapyrazoles. The electron withdrawing group may be monovalent and therefore pendant to the ring rather than in the backbone. Suitable monovalent groups are —CN, —$NO_2$, —CHO, —$CO_2R$, —$CO_2NH_2$, —P(O)(OR)$_2$, —P(O)$R_2$, —$^+PR_3$, —$^+NR_3$, —$^+SR_2$, —F and —$CF_3$.

The above mentioned monovalent and divalent electron withdrawing groups possess the characteristic of being electron withdrawing primarily because of constituents of the group with relatively high electronegativity, such as F, O, N, and S. More complex electron withdrawing groups comprise the above mentioned divalent groups in various combinations with aryl groups.

The use of such starting materials, particularly combinations of activated diaryl halides and aromatic diols, to prepare high molecular weight linear polymers has been described previously. One important difference in the present invention is that the starting materials are added continuously, or in small portions at regular intervals, during the reaction, as opposed to adding them in one portion at the beginning. It is important not to add the reactants so rapidly as to produce linear products, since linear products limit the ultimate molecular weight obtainable when the desired cyclic products are polymerized. In the present invention the reactive intermediate is present in low concentrations and can cyclize at a rate faster than it can react intermolecularly to form a longer chain. The ultimate concentration of cyclic product can be high, as no ring opening occurs under these reaction conditions.

Although pure materials of a single ring size can be isolated, for the purposes of polymerization the mixtures are more desirable because they are fluid at lower temperatures. It is also possible to combine the cyclic oligomers with high molecular weight linear polymers in order to produce a mixture with relatively low melt viscosity.

Under some conditions, mixtures of cyclic poly(aryl ether) oligomers and linear poly(aryl ether) oligomers may be obtained, wherein there is at least 10 percent by weight of the cyclic oligomers.

The reaction is carried out by gradually adding solutions of the organic reactants into a reaction medium of one or more substantially inert solvents that dilute and disperse the reactants. The reaction is desirably carried out under an inert atmosphere, and a preferred atmosphere is nitrogen. The reaction medium may contain the base in solution when the addition of the organic reactants is started. Preferred bases are alkali metal hydroxides, and especially preferred are potassium hydroxide and sodium hydroxide.

High boiling dipolar aprotic solvents boiling in the range of about 50° C. to about 250° C., are suitable for preparation of solutions of the activated aryl halides, and may also be employed as the reaction medium, or as a component thereof. In the reaction medium this solvent may optionally be mixed with a solvent which forms an azeotrope with water. Preferred dipolar aprotic solvents are dimethyl sulfoxide, tetramethylsulfone, N-alkylpyrrolidinones, N,N-dialkylacetamides, N,N-dialkylformamides, tetralkyl ureas and ethers of structure R-(OCH$_2$CH$_2$-)$_n$-OR where n is 1 to 3 and R is a hydrocarbyl of 1 to 6 carbons. Especially preferred are N,N-dimethylacetamide, N-methylpyrrolidinone and dimethyl sulfoxide. For the aromatic diol and the base a polar solvent is preferred, which may be water, or a mixture of polar solvents. Suitable azeotroping solvents include hydrocarbons of from 5 to 20 carbons, optionally substituted with halogens. Preferred azeotroping solvents include chlorobenzene, xylenes, toluene benzene, hexane, heptane and octane. The most preferred azeotroping solvents are toluene, benzene and hexane.

Gradual addition over times as long as ten days keep concentrations of reactants and reactive intermediates low. Suitable total reaction times range from about 1 hour to about 10 days, with the preferred reaction times being from 4 hours to 7 days. The time of addition of the organic reactants can be from about 10 to about 99 per cent of the total reaction time, with a preferred range being from 20 to 90 per cent of the total reaction time.

A suitable range for the concentration of all organic reactants after the addition is complete is from about 0.01 molar to about 2 molar, with a preferred concentration range being 0.01 to 0.5 molar, and the most preferred range being 0.01 to 0.2 molar.

The reaction medium is conveniently heated to a temperature at or near reflux temperature of the solvent mixture, and maintained at that temperature for the course of the reaction. A suitable range of temperatures for the reaction is from about 50° C. to about 200° C., with 50° C. to 180° C. being preferred, while from 90° C. to 180° C. is the most preferred.

The following examples are illustrative of this invention and are not intended to limit its scope.

EXAMPLE 1

A 2 L three necked flask equipped with a thermometer, a Dean-Stark trap and condenser, and a nitrogen inlet was charged with 750 mL dimethyl sulfoxide (DMSO) and 225 mL toluene. After heating the solution to reflux (140° C. pot temperature, 127° C. distillation temperature), solutions of $FC_6H_4SO_2C_6H_4F$ in DMSO (1M, 60 mL) and aqueous KOH (2M, 60 mL) were added in approximately 5 mL portions at a rate of 1 mL/hour for the difluoride, and 2 mL/hour for the hydroxide solution. The reaction was refluxed for an additional 48 hours, and then the solvent was evaporated. The residue was washed four times with approximately 150 mL hot $CHCl_3$. The combined solutions were evaporated, and the light tan solid was placed in a vacuum oven at 140° C. overnight to give 7.613 g (55% yield) of a mixture of cyclic poly(ether sulfones) with $(C_6H_4-SO_2-C_6H_4-O)$ repeat units. The inherent viscosity of this mixture was 0.06 dL/g at 25.0° C. in DMAC at 0.5 g/dL, which is to be compared with 0.36 dL/g for high molecular weight linear poly(ether sulfone) (Victrex ® PES 3600G) under the same test conditions. The $CHCl_3$ insoluble residue contained additional cyclic products which were unrecovered.

EXAMPLE 2

A 1 L three necked flask equipped with a thermometer, a Dean-Stark trap and condenser, and a nitrogen inlet was charged with 500 mL dimethyl acetamide (DMAC), diphenyl sulfone (235.9 mg) as an internal standard for analysis by liquid chromatography, and 125 mL toluene. Solutions of $F-C_6H_4-SO_2-C_6H_4-F$ (0.50M in DMAC) and $HO-C_6H_4-SO_2-C_6H_4-OH$ plus NaOH (0.50M and 1.00M respectively, in water) were prepared. After heating the solution to reflux, 4 mL of each solution was added immediately, after 21 hours, and after 50 hours of reflux. After a total of 66.4 hours, 1 mL of acetic acid was added and the solvent was evaporated to approximately 5 mL of a milky white suspension. The oil was boiled with 100 mL toluene which was filtered and evaporated. Analysis by liquid chromatography of the crystalline residue revealed a single peak. The infrared, $^1H$ and $^{13}C$ NMR, and mass spectra (m/e 928) are consistent with the structure $(C_6H_4-SO_2-C_6H_4-O)_4$. This substance could be polymerized to high molecular weight poly(ether sulfone), providing further confirmation for this structure. The toluene soluble portion was shown to be a mixture of cyclic oligomers of structure $(C_6H_4-SO_2-C_6H_4-O)_n$, where n is an even integer starting at 4 (4, 6, 8 . . . ).

EXAMPLE 3

A 1 L three-necked flask equipped with a thermometer, a Dean-Stark trap and condenser, and a nitrogen inlet was charged with 1 L dimethyl acetamide (DMAC), diphenyl sulfone (216.3 mg) as an internal standard for analysis by liquid chromatography, and 250 mL toluene. Solutions of $F-C_6H_4-CO-C_6H_4-F$ (0.50M in DMAC) and KOH (2.00M in water) were prepared. Over the course of 7 days, 28 mL of the KOH solution and 32 mL of the difluoride solution were added. After an additional day, 4 mL of acetic acid was added and the reaction was filtered to remove salt and the solvent was evaporated. The residue was boiled with 100 mL ethyl acetate which removes linear oligomers. This residue was dissolved in hot DMSO, filtered, and allowed to cool. The crystalline powder which precipitated was dried overnight at 140° C. in a vacuum oven. The $^1H$ and $^{13}C$ NMR, and mass spectra (m/e 784) are consistent with the structure $(C_6H_4-CO-C_6H_4-O)_4$.

EXAMPLE 4

Cyclic Polyether Ketone from Bisphenol A and 1,3-Bis(4-fluorobenzoyl)benezene

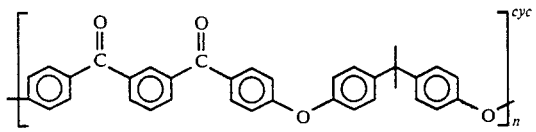

A 1 L three-necked flask equipped with a Dean-Stark trap and condenser, a thermometer, a nitrogen inlet, and magnetic stirring was charged with 450 mL DMSO (dimethyl sulfoxide) and 130 mL of toluene. After the solvents were heated to reflux (140° C. pot temperature), two solutions containing the monomers were added simultaneously using a syringe pump. The first solution was an aqueous solution of bisphenol A (0.125M) and NaOH (0.250M). The second was a solution of 1,3-bis-(4-fluorobenzoyl)benzene (0.125M) in 50/50 (v/v) DMSO/N-methylpyrrolidinone. The addition continued (rate 10 mL/hour) until 58.5 mL of both solutions were added. After an additional 18 hours of reflux (pot temperature 155°–160° C.) the reaction was allowed to cool and poured into 2 L water. The resultant mixture was extracted twice with 750 mL of 2-butanone. A layer of powder which formed at the interface of the two phases was isolated by filtration. This powder (1.321 g), a mixture of cyclics with a degree of polymerization (DP) of 1 and 2, was recrystallized from chloroform to give a single oligomer with a DP of 2 (melting point 364° C., mass spectrum: 1020 m/e). The combined organic extracts were allowed to partially evaporate, yielding an 0.906 g of solid which also consisted of a mixture of cyclics. Recrystallization from chloroform by slow solvent evaporation yielded a pure cyclic oligomer with a DP of 1 (mp 343° C., mass spectrum: 510 m/e). The total yield of cyclics was 60 percent.

EXAMPLE 5

Polymerization of Cyclic Poly(Ether Ketone)

A quantity of the cyclic poly(ether ketone) oligomers shown in the previous example (15 mg) were dissolved in 1 mL chloroform and treated with sufficient CsF solution (1 mg/mL) to give a 0.5 to 1.0 percent (w/w) suspension. the solvents were then evaporated and the solid was heated to temperatures ranging from 300° to 365° C. for about 1 hour. The resultant polymer had a glass transition temperature of 151° C., comparable to that reported (153° C.) for the high molecular weight linear polymer.

EXAMPLE 6

Cyclic Poly(Aryl Ether Nitrile) from Resorcinol and 2,6-Difluorobenzenenitrile

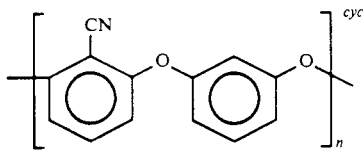

A 1 L three-necked flask equipped with a Dean-Stark trap and condensor, a thermometer, a nitrogen inlet, and magnetic stirring was charged with 400 mL N-methylpyrrolidinone, 150 mL of toluene, and 3.45 g (0.025 mole) potassium carbonate. After the solvents were heated to reflux (166° C. pot temperature), two separate 0.40M solutions of the monomers (resorcinol and 2,6-difluorobenzenenitrile) in N-methylpyrrolidinone were added simultaneously using a syringe pump. The addition continued (rate 15 mL/hour) until 50 mL of both solutions were added. During an additional hour of reflux the pot temperature was raised to 200° C. by draining toluene from the Dean-Stark trap. The reaction mixture was poured into 1 L water which was then neutralized with aqueous 1M HCl. The precipitate was filtered, washed with methanol, and treated with boiling chloroform. A pure cyclic oligomer with a DP of 4 (0.592 g, mp 397° C., mass spectrum: 836 m/e, elemental analysis: found C 74.41, H 3.41, N 6.58, calculated C 74.64, H 3.37, N 6.70) precipitated from the chloroform solution on cooling. Slow evaporation of the mother liquor afforded a second crop of crystals (0.21 g) which was a pure cyclic oligomer with a DP of 3 (mp 451° C., mass spectrum: 627 m/e, elemental analysis: found C 74.71, H 3.41, N 6.75, calculated C 74.64, H 3.37, N 6.70).

EXAMPLE 7

Preparation of Cyclic Oligomers from Hexafluorobenzene and Bisphenol A

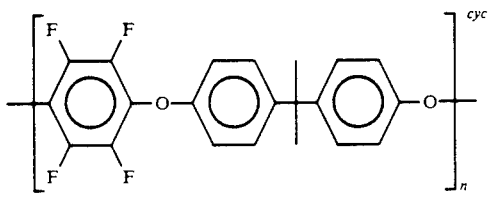

A 250 mL three-necked flask equipped with a Dean-Stark trap and condensor, a thermometer, a nitrogen inlet, and magnetic stirring was charged with 150 mL DMSO and 25 mL of benzene. After the benzene was distilled off to dehydrate the DMSO, two solutions containing the monomers were added simultaneously using a syringe pump at a pot temperature of 90° C. The first solution contained bisphenol A (5.7327 g, 1.141M) and KOH (2.35M) in DMSO/water (3/1 v/v). The second was a solution of hexafluorobenzene (1.141M) in benzene. The addition continued (rate 3.4 mL/hour) until 22 mL of both solutions were added. After an additional 15 hours of heating the reaction was allowed to cool and poured into 1 L water. The resultant mixture was extracted twice with 200 mL toluene. The combined toluene extracts were washed with 150 mL water, dried with $MgSO_4$, filtered, and evaporated. The resultant white solid was placed in a vacuum oven overnight at 120° C. to give 8.5 g crude product, which consisted of a mixture of cyclic oligomers and a high molecular weight polymer. A portion of this solid (5.2 g) was dissolved in 35 mL of acetone and precipitated with 35 mL of methanol. The suspension was filtered and the white solid was dried to give 1.32 g (25 percent yield) of a mixture of pure, low molecular weight cyclic oligomers. A single cyclic oligomer with a DP of 2 was isolated from this mixture using preparative thin layer chromatography (90/10 hexane/ethyl acetate) (mass spectrum with chemical ionization (methane): 749 m/e M+1.

EXAMPLE 8

Preparation of Cyclic Oligomers from Hexafluorobenzene and Bisphenol A

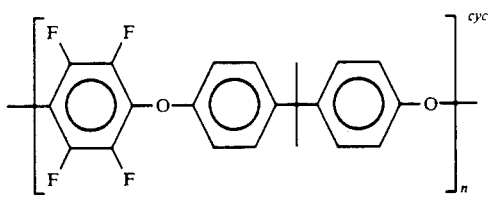

The above example was repeated using hexafluorobenzene (14.8873 g, 80.0 mmole) bisphenol A (18.2632 g, 80.0 mmole) KOH (9.5208 g, 170 mmole). The monomers were added over a 22 hour period, and heating was continued for an additional 4.5 hours. After a similar isolation procedure, 19.90 g of a mixture of cyclics and high molecular weight polymer was obtained (69 percent yield). A mixture of cyclics (6.1 g) was obtained by precipitation from acetone solution by addition of methanol as before.

EXAMPLE 9

Cyclic Poly Ether Sulfone Synthesis

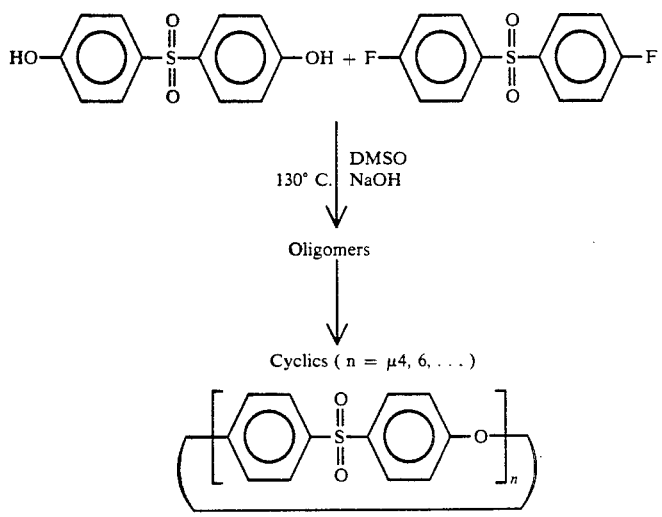

Procedure:

To a 5 L, 3-necked, round-bottom flask equipped with a thermometer, air powered stirrer, Dean-Stark trap with attached water-cooled condenser and nitrogen inlet, and a syringe pump apparatus, is added 1500 mL dimethyl sulfoxide and 800 mL toluene. This is heated to reflux (130° to 135° C.). (The amount of toluene should be adjusted to maintain this reflux temperature.) At this point, 100 mL of a 0.5M solution of 4-fluorophenyl sulfone (0.05 mol; 12.71 g) and, as an internal standard, benzophenone (0.0055 mol; 0.9945 g) in DMSO is added simultaneously with 100 mL of a 0.5M aqueous solution of the sodium salt of 4,4′-sulfonyldiphenol (0.05 mol; 12.51 g of 4,4′-sulfonyldiphenol with 20 mL of 5.0N aqueous sodium hydroxide solution) at a flow rate of 20 mL/hr. Water is continually removed from the refluxing mixture by azeotropic distillation and drained from the Dean/Start trap. During this time, the temperature should be carefully monitored. Additional toluene may be added to keep reflux temperature constant.

The flask contents are refluxed for 20 more hours. At the end of this time, a sample is analyzed by HPLC (using a ODS Hypersil, 5 μm, 100×2.1 mm column). The yields of n=4, 6, 8, and 10 cyclics are calculated on the basis of the internal standard. The yields of cyclic PES are: 21 percent of the n=4 isomer, 9 percent of the n=6 isomer, 4 percent of the n=8 isomer, and 5 percent of the n=10 isomer. The total yield of cyclic PES is 39 percent. The high molecular weight polymer accounts for 17 percent yield. The mixture is cooled and 5 mL of acetic anhydride is added.

The solution is then evaporated to approximately 150 mL. The residue is precipitated in water and the solid is washed with methanol. This solid is dried in air for several hours, then in a vacuum oven at 80° C. for several more hours.

The crude product is added to 100 mL. dimethylformamide to dissolve high molecular weight polymer and low molecular weight linear oligomers. The insoluble white powder remaining is isolated and amounts to 3.47 g (15.0% yield). HPLC analysis shows this is the 4-membered cyclic ether sulfone and a trace of 6-membered cyclic. The high molecular weight polymer is absent.

The mother liquor is evaporated to dryness and the residue is subjected to the isolation procedure again to recover additional 4-membered cyclic oligomer (1.07 g; 4.6 percent yield). The total isolated yield of 4-membered cyclic is thus 4.54 g (19.6 percent yield).

What is claimed is:

1. A cyclic poly(aryl ether) oligomer corresponding to the formula:

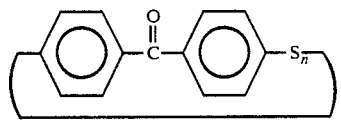

wherein n is an integer from 1 to about 20.

2. A cyclic poly(aryl ether) oligomer selected from the group consisting of:

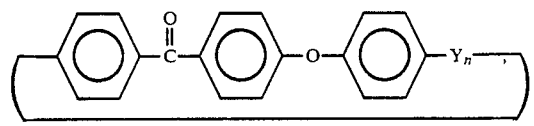

and

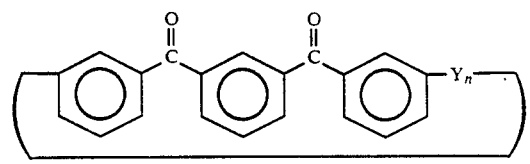

wherein Y is divalent oxygen or divalent sulfur, and n is an integer from 1 to about 20.

3. A cyclic poly(aryl ether) oligomer represented by the formula:

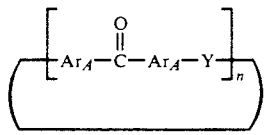

wherein n is an integer from 1 to about 20, and ArA is selected from the group consisting of:

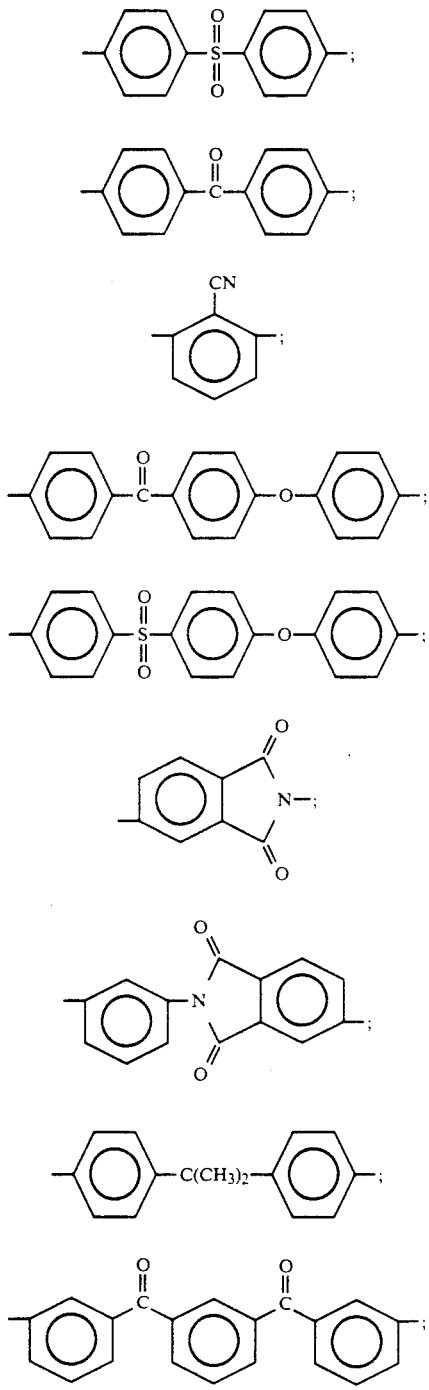

and

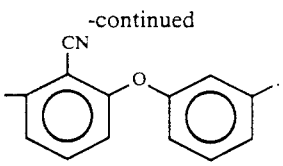

4. A cyclic poly(aryl ether) oligomer represented by the formula:

where each Y is divalent oxygen or divalent sulfur, each Ar is an aromatic diradical which comprises one or more $C_6$ to $C_{20}$ arylene groups attached by means of a divalent electron withdrawing group which is in the backbone of the oligomer, said divalent electron withdrawing group being selected from the group consisting of: $-SO_2-$, $-CONH-$, $-CONR-$, $-^+NR_2-$, $-^+PR_2-$, $-^+SR-$, $-P(O)R-$, $-C_6F_4-$, $-C_6F_4C_6F_4-$, $-C(CF_3)_2-$, $-CHCH-$, $-N=N-$, $-CHNNCH-$, imidazole, oxazole, pyrazole, isoxazole and oxapyrazole, where R is a hydrocarbyl radical of 1-12 carbon atoms, and n is an integer from 1 to about 20, with the proviso that for integer values of n equal to 1 or 2, all linkages between independent aromatic rings comprise at least one atom.

5. A cyclic poly(aryl ether) oligomer represented by the formula:

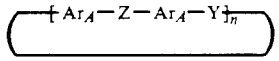

wherein each Y is divalent oxygen or divalent sulfur, Z is an electronegative group selected from the group consisting of: $-SO_2-$, $-CONH-$, $-CONR-$, $-^+NR_2-$, $-^+PR_2-$, $-^+SR-$, $-P(O)R-$, $-C_6F_4-$, $-C_6F_4C_6F_4-$, $-C(CF_3)_2-$, $-CHCH-$, $-N=N-$, $-CHNNCH-$, imidazole, oxazole, pyrazole, isoxazole and oxapyrazole, where R is a hydrocarbyl radical of 1-12 carbon atoms, each $Ar_A$ is a $C_6$-$C_{20}$ aromatic diradical, and n is an integer from 1 to about 20.

6. A cyclic poly(aryl ether) oligomer according to claim 5 selected from the group consisting of:

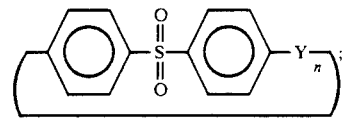

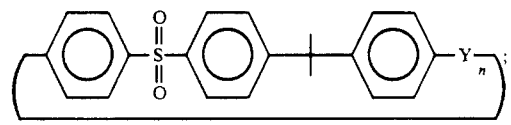

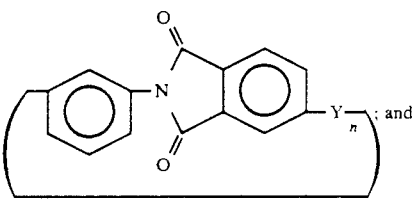

; and

-continued

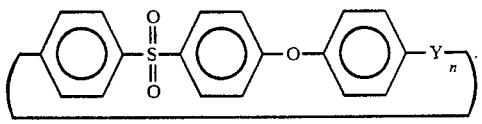

7. A cyclic poly(aryl ether) oligomer according to claim 5 wherein ArA is selected from the group consisting of:

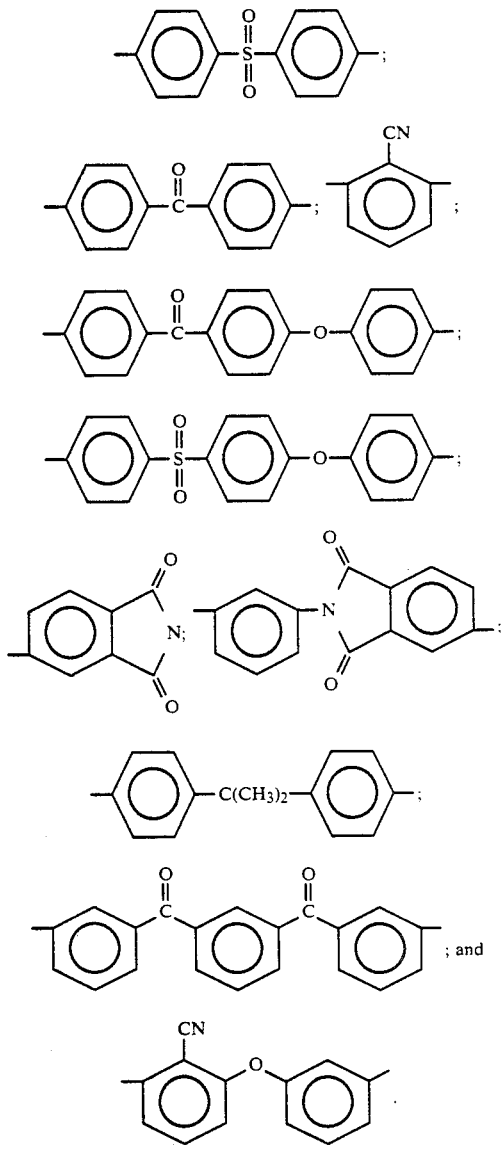

8. A cyclic poly(aryl ether) oligomer represented by the formula:

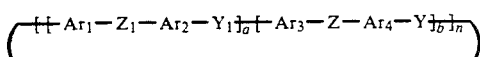

where each $Y_1$ and $Y$ are divalent oxygen or divalent sulfur; n is an integer from 1 to about 20; $Z_1$ is —$SO_2$—, —CO—, —CONH—, —CONR—, —$^+NR_2$—, —$^+PR_2$=, —$^+SR$—, —P(O)R—, —$C_6F_4$—, —$C_6F_4C_6F_4$—, —$C(CF_3)_2$—, —CHCH—, —N=N—, —CHNNCH—, imidozole, oxazole, pyrazole, isoxazole or oxapyrazole, where R is a hydrocarbyl radical of 1-12 carbon atoms; Z is —$SO_2$—, —CONH—, —CONR—, —$^+NR_2$—, —$^+PR_2$=, —$^+SR$—, —P(O)R—, —$C_6F_4$—, —$C_6F_4C_6F_4$—, —$C(CF_3)_2$—, —CHCH—, —N=N—, —CHNNCH—, imidozole, oxazole, pyrazole, isoxazole or oxapyrazole, where R is a hydrocarbyl radical of 1-12 carbon atoms; $Ar_1$, $Ar_2$, $Ar_3$ and $Ar_4$ are $C_6$-$C_{20}$ arylene groups; and a and b are integers from 1 to 3.

9. A cyclic poly(aryl ether) oligomer which is represented by the formula:

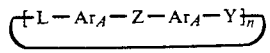

where each Y is divalent oxygen or divalent sulfur; n is an integer from 1 to about 20 with the proviso that for integer values of n equal to 1 or 2 all linkages between independent aromatic rings comprise at least one atom; Z is —$SO_2$—, —CO—, —CONH—, —CONR—, —$^+NR_2$—, —$^+PR_2$=, —$^+SR$—, —P(O)R—, —$C_6F_4$—, —$C_6F_4C_6F_4$—, —$C(CF_3)_2$—, —CHCH—, —N=N—, —CHNNCH—, imidozole, oxazole, pyrazole, isoxazole or oxapyrazole, where R is a hydrocarbyl radical of 1-12 carbon atoms; and each Ar is an arylene group containing at least one aromatic ring and L is selected from the group consisting of;

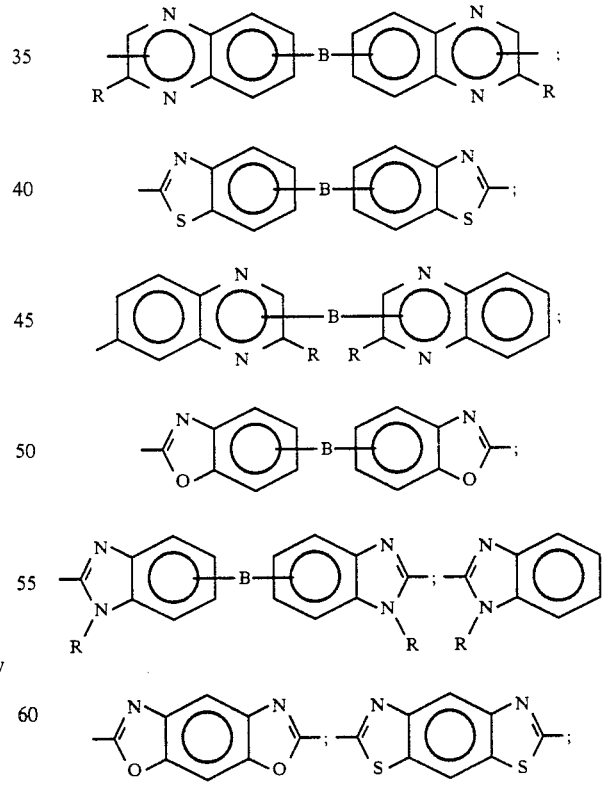

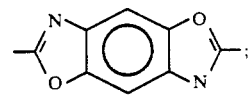

27

-continued

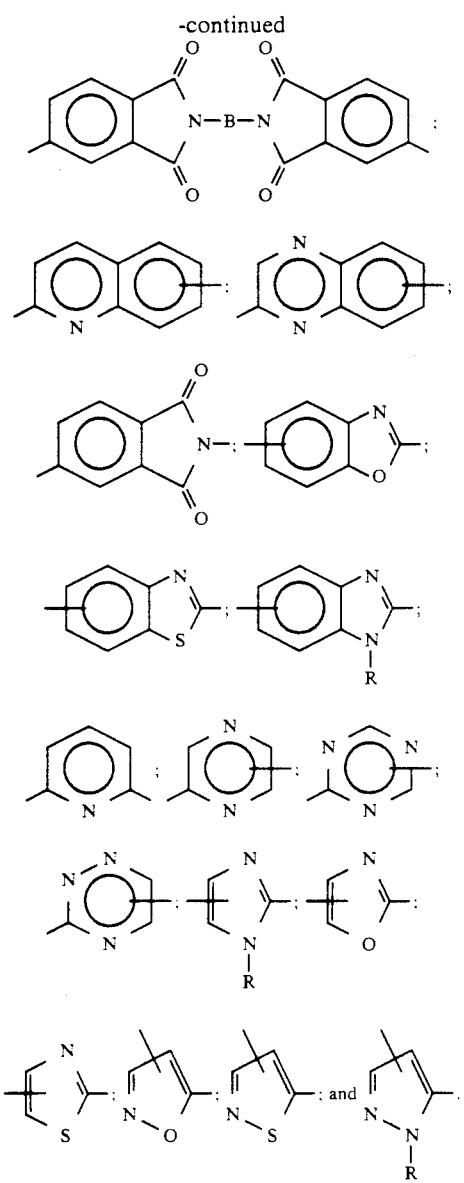

10. A cyclic poly(aryl ether) oligomer represented by the formula:

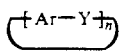

where each Y is a divalent oxygen or divalent sulfur, each Ar is an aromatic diradical which comprises one or more $C_6$ to $C_{20}$ arylene groups having at least one electron withdrawing group attached to an aromatic ring, said electron withdrawing group being selected from the group consisting of: —CN, —NO$_2$, —CHO, —CO$_2$R, —CO$_2$NH$_2$, —F, —CF$_3$, —P(O)R$_2$, —$^+$PR$_3$,

28

—$^+$NR$_3$, —$^+$SR$_2$, imidazole, oxazole, pyrazole, isoxazole, and oxapyrazole, where R is a hydrocarbyl radical of 1-12 carbon atoms, and n is an integer from 1 to about 20 with the proviso that for integer values of n equal to 1 or 2 all linkages between independent aromatic rings comprise at least one atom.

11. A cyclic poly(aryl ether) oligomer according to claim 10 where each Ar comprises only one aromatic ring.

12. A cyclic poly(aryl ether) oligomer as described in claim 10 selected from the group consisting of:

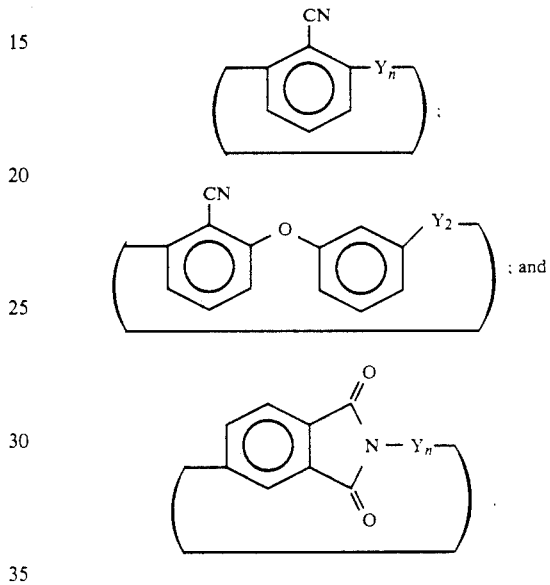

13. A composition which comprises a mixture of:
(a) at least 10% of one or more cyclic poly(aryl ether) oligomers represented by the formula:

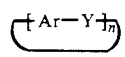

and
(b) up to 90% of one or more linear poly(aryl ether) polymers wherein the repeating unit is

where each Y is divalent oxygen or divalent sulfur, each Ar is an aromatic diradical which comprises one or more $C_6$ to $C_{20}$ arylene groups and has at least one electron withdrawing group attached to an aromatic ring, n is an integer from 1 to about 20 with the proviso that for integer values of n equal to 1 or 2 all linkages between independent aromatic rings comprise at least one atom, and m is an integer greater than 20.

* * * * *

UNITED STATES PATENT AND TRADEMARK OFFICE
CERTIFICATE OF CORRECTION

PATENT NO. : 5,264,538

DATED : November 23, 1993

INVENTOR(S) : Michael J. Mullins; Edmund P. Woo; Kimberly E. Balon; Daniel J. Murray; Cheng-Cheng C. Chen It is certified that error appears in the above-indentified patent and that said Letters Patent is hereby corrected as shown below:

Col. 27, line 58, following "-CF$_3$" insert therefor -- -P(O)(OR)$_2$ --.

UNITED STATES PATENT AND TRADEMARK OFFICE
CERTIFICATE OF CORRECTION

PATENT NO. : 5,264,538

DATED : November 23, 1993

INVENTOR(S) : Michael J. Mullins; Edmund P. Woo; Kimberly E. Balon; Daniel J. Murray; Cheng-Cheng C. Chen It is certified that error appears in the above-indentified patent and that said Letters Patent is hereby corrected as shown below:

Col. 28, lines 21-26, delete the following formula:

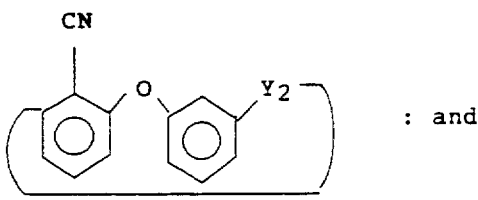 : and and insert therefor the following formula:

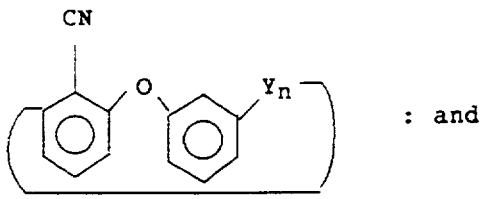 : and

Signed and Sealed this

Eighth Day of November, 1994

Attest:

BRUCE LEHMAN

*Attesting Officer*  *Commissioner of Patents and Trademarks*